United States Patent
Fritchie

(10) Patent No.: US 8,035,485 B2
(45) Date of Patent: Oct. 11, 2011

(54) SYSTEM FOR TRACKING VESSELS IN AUTOMATED LABORATORY ANALYZERS BY RADIO FREQUENCY IDENTIFICATION

(75) Inventor: Patrick P. Fritchie, Southlake, TX (US)

(73) Assignee: Abbott Laboratories, Abbott Park, IL (US)

( * ) Notice: Subject to any disclaimer, the term of this patent is extended or adjusted under 35 U.S.C. 154(b) by 504 days.

(21) Appl. No.: 12/274,479

(22) Filed: Nov. 20, 2008

(65) Prior Publication Data

US 2010/0123551 A1 May 20, 2010

(51) Int. Cl.
  *H04Q 5/22* (2006.01)
(52) U.S. Cl. .................. 340/10.1; 340/572.1; 340/572.7
(58) Field of Classification Search .................. 340/10.1, 340/572.1–572.8; 235/375, 385
See application file for complete search history.

(56) References Cited

U.S. PATENT DOCUMENTS

| | | | |
|---|---|---|---|
| 4,735,778 A | 4/1988 | Maruyama et al. | |
| 6,879,876 B2 | 4/2005 | O'Dougherty et al. | |
| 7,275,682 B2 * | 10/2007 | Excoffier et al. | 235/375 |
| 7,411,508 B2 * | 8/2008 | Harazin et al. | 340/572.7 |
| 7,602,293 B2 * | 10/2009 | Taki et al. | 340/572.1 |
| 2004/0258565 A1 | 12/2004 | Watari | |
| 2005/0019943 A1 | 1/2005 | Chaoui et al. | |
| 2005/0036907 A1 | 2/2005 | Shoji | |
| 2005/0106747 A1 | 5/2005 | Chaoui et al. | |
| 2005/0186114 A1 | 8/2005 | Reinhardt et al. | |
| 2005/0242963 A1 | 11/2005 | Oldham et al. | |
| 2006/0018996 A1 * | 1/2006 | Pollock et al. | 426/19 |
| 2006/0213964 A1 * | 9/2006 | Excoffier et al. | 235/375 |
| 2007/0036686 A1 * | 2/2007 | Hatamian et al. | 422/102 |
| 2007/0080787 A1 * | 4/2007 | Taki et al. | 340/10.1 |
| 2008/0024301 A1 | 1/2008 | Fritchie et al. | |
| 2009/0322486 A1 * | 12/2009 | Gerstel | 340/10.1 |

FOREIGN PATENT DOCUMENTS

| | | |
|---|---|---|
| WO | 2004/044824 A2 | 5/2004 |
| WO | 2005/024385 A2 | 3/2005 |
| WO | WO2008014117 A2 | 1/2008 |

OTHER PUBLICATIONS

Avoine, et al., RFID Traceability: A Multilayer Problem, Ecole Polytechnique Federale De Lausanne [online], 2005 [retrieved on May 14, 2009]. Retrieved from the Internet: <URL: http://lasecwww.epfl.ch/~gavoine/download/papers/AvoineO-2005-fc.pdf>, pp. 1-15.

Microtiter plate—Wikipedia, the free encyclopedia [online], [retrieved on May 4, 2009]. Retrieved from the Internet: <URL: http://en.wikipedia.org/wiki/Microtiter_plate>, pp. 1-3.

(Continued)

*Primary Examiner* — Eric M Blount
(74) *Attorney, Agent, or Firm* — Timothy P. Lucier

(57) ABSTRACT

A system for automation of laboratory analyzers that utilizes radio frequency identification (RFID) tags and radio frequency identification (RFID) readers to identify containers and vessels, and the contents thereof, that are employed in the system. Radio frequency identification tags, conforming to the guidelines of ISO 18000 and either of ISO 14443 or ISO 15693, are positioned on the items of interest, such as, for example, reagent containers, sample containers, and microplates. These tags can be read by and written to by a stationary antenna connected to a radio frequency identification reader. Reading of radio frequency identification tags and writing to radio frequency identification tags are controlled by software.

38 Claims, 7 Drawing Sheets

OTHER PUBLICATIONS

Attenuator Dissipation—Microwave Encyclopedia—Microwaves101.com [online]. Mar. 26, 2007 [retrieved on May 5, 2009]. Retrieved from the Internet: <URL: http://www.microwaves101.com/encyclopedia/attenuatordiss.cfm>, pp. 1-6.

Attenuators—Microwave Encyclopedia—Microwaves101.com [online]. Apr. 21, 2009 [retrieved on May 4, 2009]. Retrieved from the Internet: <URL: http://www.microwaves101.com/encyclopedia/attenuators.cfm>, pp. 1-6.

Leong, et al., Positioning Analysis of Multiple Antennas in a Dense RFID Reader Environment, Proceedings of the International Symposium on Applications and the Internet Workshops (Saint Workshops 2006), (2006) pp. 56-59.

Song, et al., A proximity-based method for locating RFID tagged objects, Advanced Engineering Informatics, Elsevier, Ltd., vol. 21, No. 4, (2007) pp. 367-376.

The PCT International Search Report, PCT/US2009/065139, Date of mailing Mar. 17, 2010.

* cited by examiner

SYSTEM FOR TRACKING VESSELS IN AUTOMATED LABORATORY ANALYZERS BY RADIO FREQUENCY IDENTIFICATION

BACKGROUND OF THE INVENTION

1. Field of the Invention

This invention relates to systems that utilize automated laboratory analyzers, and more particularly, systems that utilize automated laboratory analyzers that require identification of containers for biological samples and reagents.

2. Discussion of the Art

Previous implementations for identification of reagents and other consumable items for automated laboratory analyzers have utilized barcode technology. Barcodes have been attached to items of interest, such as, for example, reagent containers, sample containers, e.g., test tubes, and test tube racks, and selectively scanned by a barcode reader for the purpose of identification and tracking of information associated with these items.

Barcode technology has several limitations that inhibit optimally efficient architectures of automated analyzers for use in laboratories. Reading barcodes requires a direct line-of-sight from the barcode reader to the barcode. In addition, the barcode typically occupies a large portion of the surface of a reagent container or test tube. Because the barcode occupies such a large surface area, the reagent containers and the sample containers must be separated by a great distance, and, consequently, the reagent containers and the sample containers consume a large area of the analyzer. Another adverse effect of the use of a large area of the analyzer is that the range of motion for aspirating devices, such as, for example, pipettes, and refrigeration equipment must be greatly increased. Still another adverse effect of barcode technology is that barcode readers of increasing complexity must be used because the barcode readers require variable depths of field. The sizes of barcodes and the surfaces of the reagent containers and sample containers limit the amount of data that can be associated with the containers. Barcodes cannot be updated to account for changes in the amount of reagent or sample, i.e., the number of tests remaining, or the on board expiration date of the reagent after the reagent container has been opened. Furthermore, cleaning and alignment of barcode reader windows account for about half of the barcode reading problems reported in the field.

Radio frequency identification (hereinafter alternatively referred to as "RFID") technology can be used as a replacement for barcodes and barcode readers in order to promote more efficient architectures for analyzers. RFID tags can be placed on a small portion of the surface of a reagent container and read in close proximity to a RFID reader, thereby minimizing the area required of the analyzer, and further minimizing the range of motion required for aspirating devices, e.g., pipettes, and refrigeration equipment. RFID tags typically utilize silicon-based memory chips, which can contain many times more information than can barcodes. RFID tags can be written to and can be updated with information relating to the analyzer, the environment, and the reagent container, thereby providing improved functioning of the analyzer, improved chain of custody, and improved safety to consumers. RFID tags can be read in a wide range of environmental conditions, with the result that cleaning and alignment of barcodes are not required.

There have been some attempts to utilize RFID tags in the environment of automated laboratory analyzers. See, for example, U.S. Pat. No. 6,879,876; U.S. Patent Application Publication No. 2004/0258565; U.S. Patent Application Publication No. 2005/0019943; U.S. Patent Application Publication No. 2005/0036907; U.S. Patent Application Publication No. 2005/0106747; U.S. Patent Application Publication No. 2005/0186114; WO 2004/044824; and WO 2005/024385. U.S. Patent Application Publication No. 2008/0024301, incorporated herein by reference, discloses a system for automation of laboratory analyzers that utilizes radio frequency identification (RFID) tags and radio frequency identification (RFID) readers to identify containers and vessels, and the contents thereof, that are employed in the system. Radio frequency identification tags, conforming to the guidelines of ISO 18000 and either of ISO 14443 or ISO 15693, are positioned on the items of interest, such as, for example, reagent containers, sample containers, and microplates. These tags can be read by and written to by either a moving antenna connected to a RFID reader or a stationary antenna connected to a RFID reader. Reading of RFID tags and writing to RFID tags are controlled by software.

There is a desire for a system for updating data relating to samples and reagents. There is a desire for a system that enables movement of a reagent from one automated system to another in the case of the failure of an automated system or a reallocation of the workload of an automated system. There is a desire for an automated system that enables the updating of the demographics of patients, whereby the results of the assays of numerous biological samples can be correlated with various statistics associated with those patients providing the biological samples.

SUMMARY OF THE INVENTION

This invention provides a system for automation of laboratory analyzers that utilizes radio frequency identification (RFID) tags and radio frequency identification (RFID) readers to identify containers and vessels, and the contents thereof, that are employed in the system. Radio frequency identification tags, conforming to the guidelines of ISO 18000 and either of ISO 14443 or ISO 15693, are positioned on the items of interest, such as, for example, reagent containers, sample containers, and microplates. These tags can be read by and written to by a stationary antenna connected to a radio frequency identification reader. Reading of radio frequency identification tags and writing to radio frequency identification tags are controlled by software.

In one embodiment, the system includes at least one stationary radio frequency identification reader. In order for the at least one radio frequency identification reader to read data from a radio frequency identification tag associated with a container, the container is caused to move to a position proximate to, and preferably in register with, a given antenna connected to the radio frequency identification reader. The power of the radio frequency identification reader is attenuated to a level such that the given antenna is required to be in close proximity to the radio frequency identification tag, whereby the amount of noise and interference from nearby radio frequency identification tags on other containers are insufficient to adversely affect the integrity of the data received by the given antenna connected to the radio frequency identification reader.

According to one embodiment, each antenna, which is a trace on a printed circuit board, functions as a separate antenna for a radio frequency identification reader. In other words, the radio frequency identification reader is connected to a plurality of antennas, each antenna positioned at a different location. The dimensions of the antenna are important, because the dimensions of the antenna determine the density of the radio frequency energy used. The length of the antenna need not correspond to some multiple of wavelength of radio frequency energy, e.g., one-half wavelength, one-quarter wavelength.

Initially, it was believed that both the antenna connected to the radio frequency identification reader and the antenna of the radio frequency identification tag were required to have a length that was a fraction of the wavelength. Typically, antennas for receiving radio frequency signals are designed for ¼ or ½ wavelength. For example, to calculate a quarter wavelength dipole FM antenna:

$3 \times 10^8$ m/sec divided by $92 \times 10^6$ cycles/sec equals 3.26 meters. One quarter of 3.26 meters equals 0.815 meter, which is approximately 32 inches, which is the approximate size of an automobile antenna Given a frequency of 13.56 MHz, this wavelength would be 22.1 meters/cycle. Based on this value, even a very small fraction of the wavelength would require a very large antenna. Although this theory is used to design antennas for far field applications, another phenomenon was taking place in the near field region between the radio frequency identification reader and the radio frequency identification tag. Near field coupling occurs when two resonant circuits are sufficiently close so that a passive circuit could be stimulated by the active circuit. Thus, using the same frequency of 13.56 MHz, the inductance of the antenna could be matched to a capacitor and cause the circuit to resonate at 13.56 MHz, regardless of the length of the antenna. Frequency is equal to [1 divided by $2\pi$ times the square root of the product of inductance (L) and capacitance (C)].

In order to implement the system of this invention, a radio frequency identification tag can be positioned on the lowermost portion of a container. It is often desirable to position an encapsulated radio frequency identification tag on the lowermost portion of a container.

In another aspect, a method is provided whereby the system previously described can read the data from radio frequency identification tags attached to containers.

The system described herein provides the ability to aggregate read information with a container in addition to the sample identifier or the reagent identifier. For sample containers, read information, other than the sample identifier, can include (a) demographics of patients, (b) the date the sample was obtained, (c) the test(s) to be performed upon the sample, (d) the type of sample, (e) the type of container, etc. The system provides the ability to track shipping and storage conditions that may affect the integrity of a biological sample. In addition, the system can be used for writing information, such as, for example, centrifugation operations performed, aspiration operations performed, potential contamination or dilution of a sample by material carried over by the tip of an aspirating device, temperature conditions of the sample, freeze-thaw conditions of the sample, etc.

For reagent containers, read information, other than the reagent identifier, can include (a) calibration data for the reagent, (b) lot number of the reagent, (c) serial number of the reagent, (d) identification of components of the reagent, (e) identification of the assay, (f) expiration date of the reagent, (g) kit size, (h) package insert information, (i) material safety data sheet, (j) assay protocol, etc. The system provides the ability to track shipping and storage conditions that may affect integrity of a reagent. In addition, the system can be used for writing information such as (a) tests remaining, (b) on-board expiration date (after the container has been opened), (c) aspiration operations performed, and (d) potential contamination or dilution of samples and reagents by material carried over by the tip of an aspiration device, etc.

For microplates, read information, other than the microplate identifier, can include (a) manufacturing lot number of a microplate, (b) serial number of a microplate, (c) expiration date of the reagent(s) in the microplate, etc. The system provides the ability to track shipping and storage conditions that may affect integrity of the microplate. In addition, the system can be used for writing information such as (a) date used, (b) processing steps performed, (c) on-board expiration of the microplate (after the microplate has been opened), etc.

The use of a radio frequency identification system allows a more compact physical architecture than would be possible with barcode technology by eliminating line of sight and spatial separation requirements, (b) improving reliability (in extreme environments) of reading information on a container, vessel, and microplate. The use of a radio frequency identification system also enables proper physical orientation of containers, i.e., the system ensures that a given container, vessel, microplate is in the proper location prior to its use.

Radio frequency identification can be used to increase the quantity of information on the container, the vessel, or the microplate. In addition, a radio frequency identification tag can be updated; a barcode cannot be updated. Furthermore, the information can be directly linked to a database, thereby providing (a) improved functioning of automated analyzer(s) in a system, (b) improved chain of custody, i.e., improved information relating to locations occupied by a given container in the present and at times previous to the present, and (c) improved safety to patients by ensuring accurate results of assays. This information includes information relating to the analyzer, the environment, i.e., the environments experienced during shipping, storage, and usage of the contents of the container.

The system also provides the ability to positively verify a sample or identify a reagent during aspiration or dispensing, thereby enabling an operator of the system to be given physical access to samples and reagents, except for those samples and reagents currently being aspirated or dispensed. Physical access to samples or reagents currently being aspirated or dispensed should be prohibited to the operator in order to ensure the safety of the operator.

BRIEF DESCRIPTION OF THE DRAWINGS

In FIG. 8A, the antennas of the bottom layer are shown in phantom.

In FIG. 8B, the antennas of the top layer are shown in phantom.

DETAILED DESCRIPTION

Figure 1:
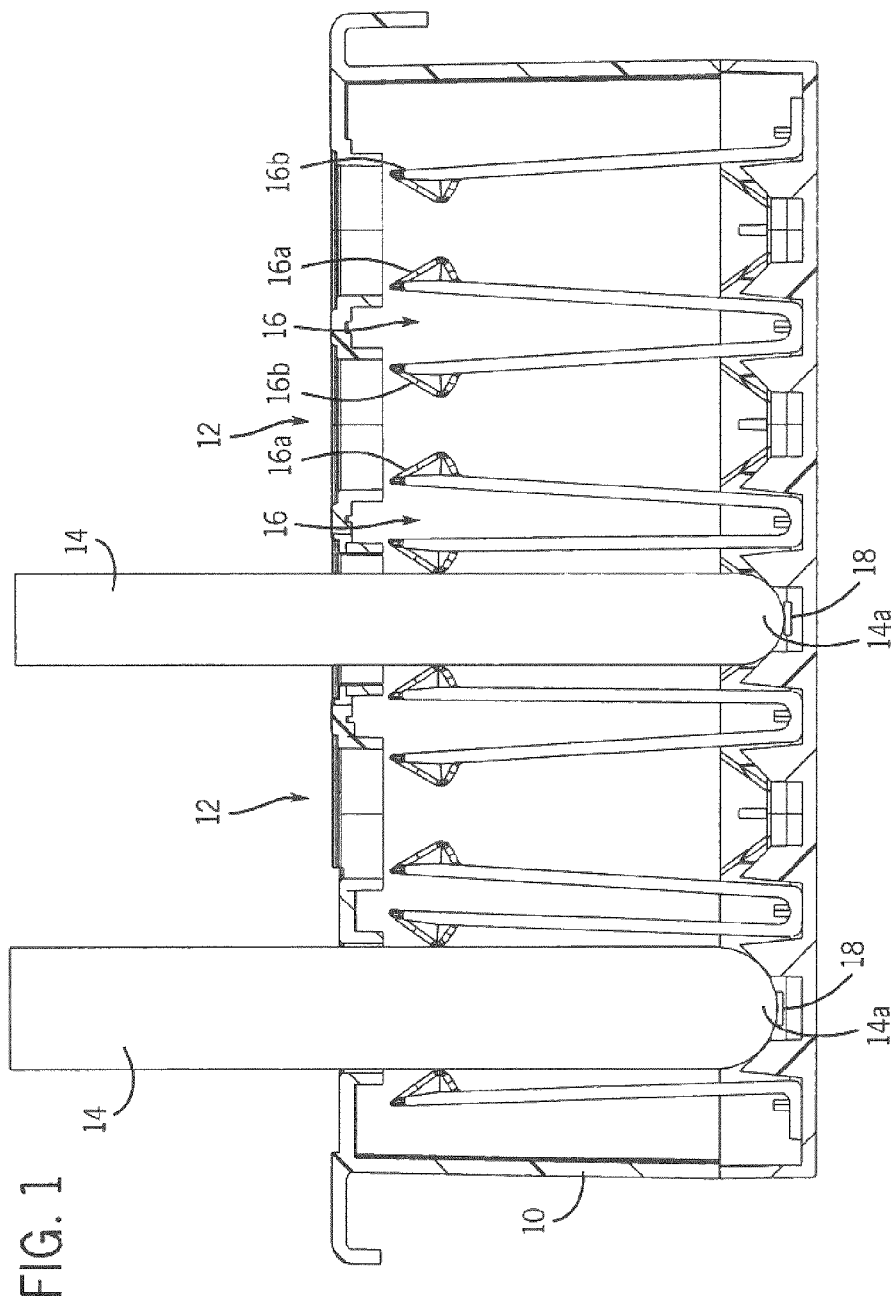
FIG. 1 is a cross-sectional view of a sample container carrier holding two sample containers, i.e., sample tubes. Radio frequency identification tags are attached to the lowermost ends of the sample tubes.

As used herein, the expression "radio frequency identification", or "RFID", is a generic term for technologies that use radio waves to automatically identify objects, such as, for example, containers for biological samples and containers for reagents for analyzing biological samples. The most common method of identification is to store a serial number that identifies the object, and perhaps other information relating to the object or contents thereof, on a microchip that is attached to an antenna. The microchip and the antenna together are called a radio frequency identification transponder or a radio frequency identification tag. The antenna enables the microchip to transmit the identification information and other information to an antenna connected to a radio frequency identification reader. The radio frequency identification reader converts the radio waves transmitted from the radio frequency identification tag into digital information that can then be passed on to computers that can make use of it.

As used herein, the expression "radio frequency identification system", or "RFID system", comprises a radio frequency identification tag made up of a microchip with an antenna, and a radio frequency identification interrogator or radio frequency identification reader with an antenna. The radio frequency identification reader sends out electromagnetic waves. The tag antenna is tuned to receive these waves. A passive radio frequency identification tag draws power from the field created by the reader and uses it to power the circuits of the microchip. The microchip then modulates the waves that the passive radio frequency identification tag sends back to the radio frequency identification reader, which converts the waves received by the radio frequency identification reader into digital data.

As used herein, microchips in radio frequency identification tags can be "read-write microchips", "read-only microchips", or "write once, read many microchips." In the case of read-write microchips, information can be added to the radio frequency identification tag or existing information can be written over when the radio frequency identification tag is within range of a radio frequency identification reader. Read-write microchips usually have a serial number that cannot be written over. Additional blocks of data can be used to store additional information about the items to which the radio frequency identification tag is attached. These radio frequency identification tags can be locked to prevent overwriting of data or encrypted to prevent the disclosure of proprietary data or disclosure of data that would compromise the privacy of a patient. Read-only microchips have information stored on them during the manufacturing process. The information on them can never be changed. Write once, read many microchips have a serial number and other data written to them once, and that information cannot be overwritten later.

As used herein, the expression "active radio frequency identification tags" have a transmitter and their own power source, typically a battery. The power source is used to run the microchip's circuitry and to broadcast a signal to a radio frequency identification reader. The microchip's circuitry can possibly perform some sort of monitoring function. "Passive radio frequency identification tags" have no battery. Instead, passive radio frequency identification tags draw power from the radio frequency identification reader, which sends out electromagnetic waves that induce a current in the tag's antenna. "Semi-passive tags" use a battery to run the microchip's circuitry, but communicate by drawing power from the radio frequency identification reader. Any of the foregoing types of radio frequency identification tags can be used in the system of this invention.

As used herein, the expression "tag collision" occurs when more than one transponder reflects back a signal at the same time, confusing the radio frequency identification reader. Algorithms can be used to "singulate" the tags.

As used herein, the term "radio frequency identification reader" or "reader" means a device having the function of providing means for communicating with a radio frequency identification tag and facilitating transfer of data to and from a radio frequency identification tag. Functions performed by a radio frequency identification reader can include quite sophisticated signal conditioning, signal sorting, parity error checking, and correction. Once the signal from a radio frequency identification tag has been correctly received and decoded, algorithms can be applied to decide whether the signal is a repeat transmission, and can then instruct the radio frequency identification tag to cease transmitting. This type of interrogation is known as "command response protocol" and is used to circumvent the problem of reading a plurality of radio frequency identification tags in a short space of time. An alternative technique involves the radio frequency identification reader looking for radio frequency identification tags with specific identities, and interrogating them in turn. It is within the scope of this invention to use a single radio frequency identification reader or a plurality of radio frequency identification readers. A radio frequency identification reader is connected to a single antenna or to a plurality of antennas.

As used herein, the expression "near field region" means the close-in region of an antenna where the angular field distribution is dependent upon the distance from the antenna. The near field is that part of the radiated field that is within a fraction of a wavelength of the antenna. As used herein, the expression "far field region" means the region outside the near field region, where the angular field distribution is essentially independent of distance from the source. If the source has a maximum overall dimension D that is large compared to the wavelength, the far-field region is commonly taken to exist at distances greater than $D^2/\lambda$ from the source, $\lambda$ being the wavelength.

As used herein, the term "microplate" means a flat plate having multiple "wells" used as small test tubes. Additional discussion of microplates can be found at "Microtiter plate—Wikipedia, the free encyclopedia" at the website http://en.wikipedia.org/wiki/Microtiter_plate.

As used herein, the expression "dimension of an antenna", and the like, refers to the measure of the planar region of the antenna, i.e., the area of the plane of the antenna. For example, if the diameter of the trace of an antenna on a printed circuit board is "d", the area of the antenna is $\pi(d/2)^2$.

As used herein, the term "trace" means a design printed on something, such as, for example, a circular antenna printed on a circuit board. A trace typically comprises a wire made of conductive material, such as, for example, copper, which wire typically has a small diameter, such as, for example, on the order of from about 0.004 inch to about 0.008 inch.

Commercially available components suitable for use in the present invention are set forth in TABLE I:

TABLE I

| Item | Supplier | Model Number |
|---|---|---|
| RFID reader | Escort Memory Systems (EMS), Scotts Valley, California | HF-CNTL-232-01 |
| RFID tags for containers for clinical chemistry analysis | Escort Memory Systems (EMS), Scotts Valley, California | HMS-112 |
| RFID tags for racks for holding sample containers | Escort Memory Systems (EMS), Scotts Valley, California | HMSP-108 |
| RFID tags for microplates | Escort Memory Systems (EMS), Scotts Valley, California | HMS-108 |
| RFID tags for containers for immunoassay analysis | Escort Memory Systems (EMS), Scotts Valley, California | LRP-P125 |
| Custom antenna board | Wavetrix, Inc. Richardson, Texas | |
| Microlab STARlet pipette (4 pipetting channels) | Hamilton Company, Reno, Nevada | 173000-001 |
| Hamilton Vector software | Hamilton Company, Reno, Nevada | |
| Hamilton labware:<br>(a) Multi-Flex Carrier Base with immunoassay, clinical chemistry, and microplate stackers<br>(b) 2 position holder for disposable tips<br>(c) 4 position holder for disposable tips<br>(d) Microplate core grippers<br>(e) bulk fluid troughs | Hamilton Company, Reno, Nevada | |
| Custom method and liquid classes for processing immunoassays and clinical chemistry assays | Abbott Laboratories, Abbott Park, Illinois | |
| Custom labware:<br>(a) immunoassay reagent storage rack with dispersing element<br>(b) clinical chemistry reagent storage rack<br>(c) microplate rotator with incubation control<br>(d) sample carrier tray and racks | Abbott Laboratories, Abbott Park, Illinois | |
| Multi-axis motion controller | Pro-Dex Oregon Micro Systems, Beaverton, Oregon | MAXp-8000 |
| Motor driver | Intelligent Motion Systems, Marlborough, Connecticut | |
| Heater controllers; Heater pads and thermistors | Watlow Electric Manufacturing Company, St. Louis, Missouri | |

Radio frequency identification tags can be permanently applied to a given component, i.e., container, either by means of a molding process or by means of a bonding process. Radio frequency identification tags applied by molding or bonding are not re-usable. However, radio frequency identification tags can be rendered re-usable by ensuring that reagent containers, sample containers, or microplates are destroyed and the radio frequency identification tags recovered.

Reading radio frequency identification tags and writing radio frequency identification tags can be performed using ISO protocols 14443, 15693, or 18000, all of which are incorporated herein by reference, or combinations of the foregoing ISO protocols. These protocols utilize a three-layer communication model:

(a) application layer
(b) communication layer
(c) physical layer.

The three-layer communication model, primarily the communication layer, will provide the functions of error detection, error correction, identity authentication, collision avoidance, etc. These functions can be considered automatic, because they are part of the protocol for enabling the radio frequency identification reader to communicate with the radio frequency identification tag.

The application layer handles the information contained in the radio frequency identification tag. Such information can include at least some of the information in TABLE II:

TABLE II

| Class of data | Specific data |
|---|---|
| Tag identifier | Unique identifier for container |
| Manufacturing data | (a) Revision number(s) of reagent(s) |
| | (b) Serial number(s) of reagent(s) |
| | (d) Component identifier(s) |
| | (e) Lot number(s) of reagent(s) |
| | (f) Stability/expiration data for reagent(s) |
| | (g) Times/dates of manufacture of reagent(s) |
| | (h) Configuration(s) of assay(s) |
| | (e.g., number of reagent containers needed) |
| | (i) Number of tests in container(s) |
| | (j) Associated components of assay(s) |
| | (k) Calibration data for assay(s) |
| | (l) Material safety data sheet |
| | (m) Assay protocol |
| | (n) Package insert |
| Shipping and storage data | (a) Temperature(s) of reagent during shipping |
| | (b) Times/dates of shipping movements and storage periods |
| | (c) Locations and dates of storage periods |
| Analyzer and usage data | (a) Times/dates of opening(s) of reagent container(s) |
| | (b) Number of aspirations from reagent container(s) |
| | (c) Carryover and potential contamination or dilution of reagent(s) or sample(s) |
| | (d) Encryption algorithms for protection of data |
| | (e) Other algorithms to ensure integrity of data |

The communication layer defines the manner whereby radio frequency identification readers and radio frequency identification tags communicate. The communication layer includes, but is not limited to, collision avoidance algorithms, parity checking algorithms, error-checking algorithms, and identification authentication algorithms. After the unique identifier of a radio frequency identification tag is known, a deterministic protocol can be used to ensure selectivity. The operation of a deterministic protocol is described, for example, in "RFID Traceability: A Multilayer Problem", Gildas Avoine and Philippe Oechslin, Ecole Polytechnique Federale De Lausanne, 2005, incorporated herein by reference.

The physical layer defines the actual interface and specifies at least the following: radio frequency (e.g., 13.56 MHz, 860 MHz, 960 MHz), modulation, data encoding, timing, etc.

The memory capacity of a radio frequency identification tag suitable for use in this invention typically ranges from about 112 to 736 bytes. This quantity of bytes can exceed those in a typical barcode label. Radio frequency identification readers and other radio frequency identification tags (as specified in ISO 18000 and either of ISO 14443 or ISO 15693) that use 16 bits for the address can support a memory capacity of up to 128 kilobytes. Memory availability can be varied, but can range to a level as high as 32 kilobytes per read operation. Thus radio frequency identification tags having more than 32 kilobytes of memory would require the reader to carry out multiple read operations.

The operational details of the system of this invention can be controlled by a computer. Furthermore, some higher-level data integrity algorithms can be implemented. An example of a higher-level data integrity algorithm is one that would indicate that reading the same radio frequency identification tag from multiple antennas is an error. Higher-level algorithms suitable for use in this invention are known to those of ordinary skill in the art High selectivity requires close proximity of reader and radio frequency identification tags. In addition, use of metal or material exhibiting metal-like properties (such as carbon impregnated plastic), are preferably avoided in the system, because metal interferes with radio frequency identification signals.

Figure 2:
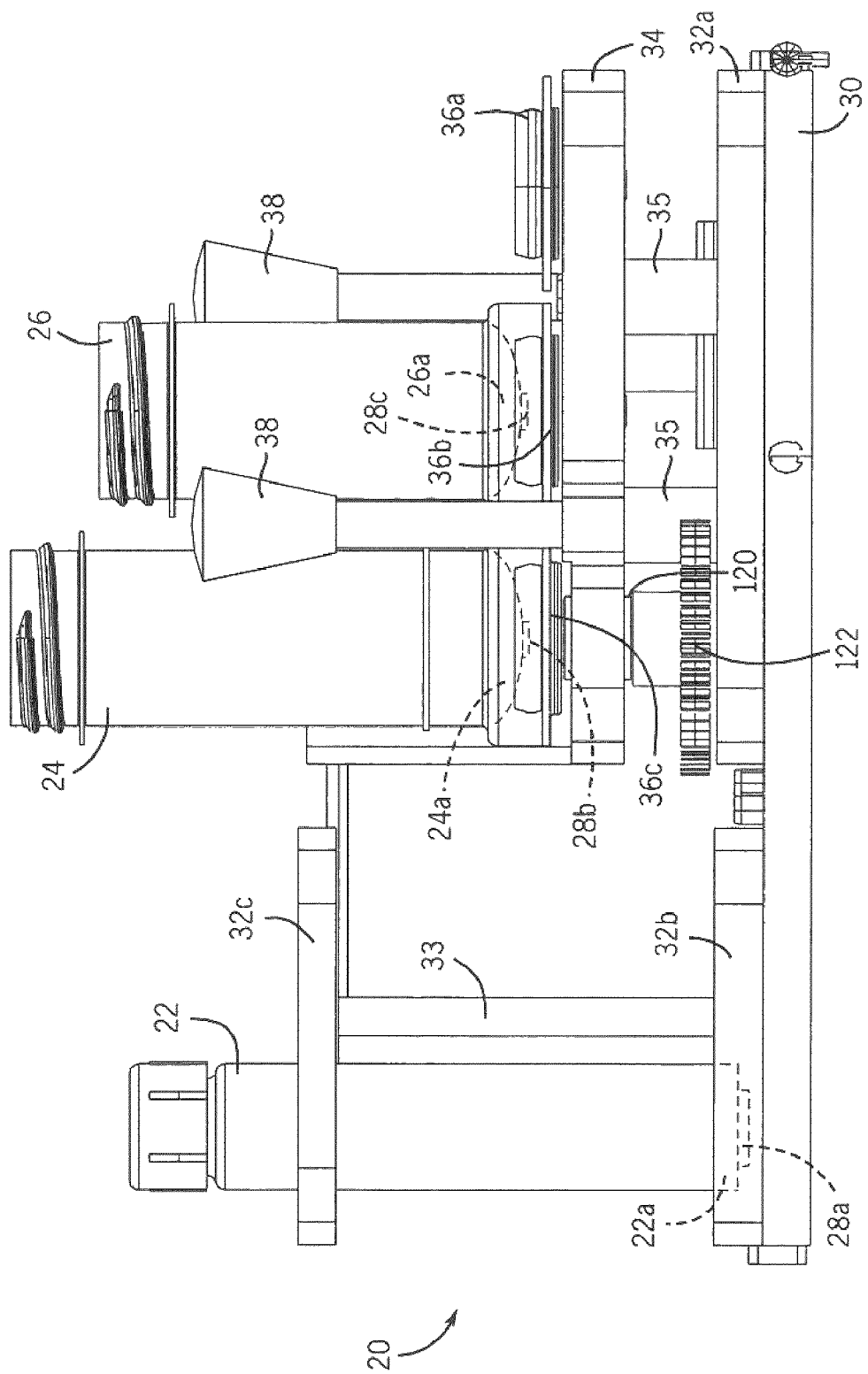
FIG. 2 is a side view in elevation showing two reagent container carriers holding three reagent containers. Radio frequency identification tags are attached to the lowermost ends of the reagent containers. The contents of one of the reagent containers shown are used in clinical chemistry assays. The contents of two of the reagent containers shown are used in immunoassays.
Figure 3:
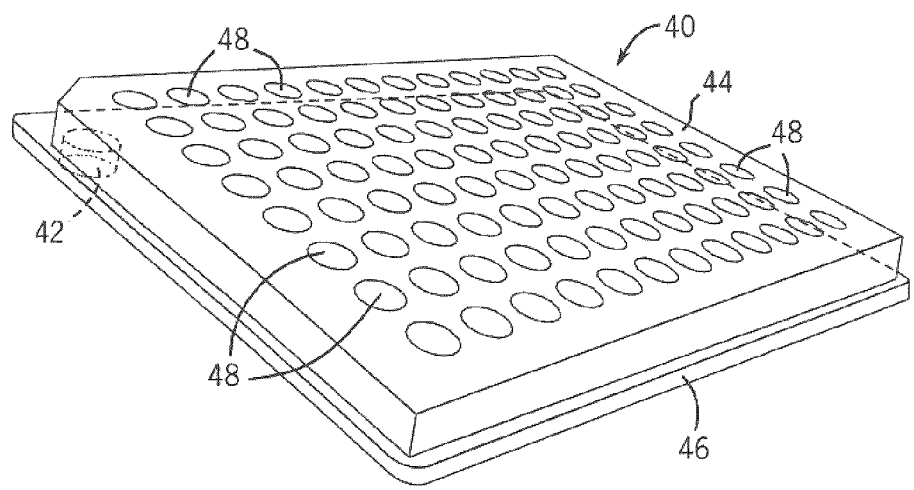
FIG. 3 is a perspective view showing a microplate. A radio frequency identification tag is attached to the base of the microplate.
Figure 5:
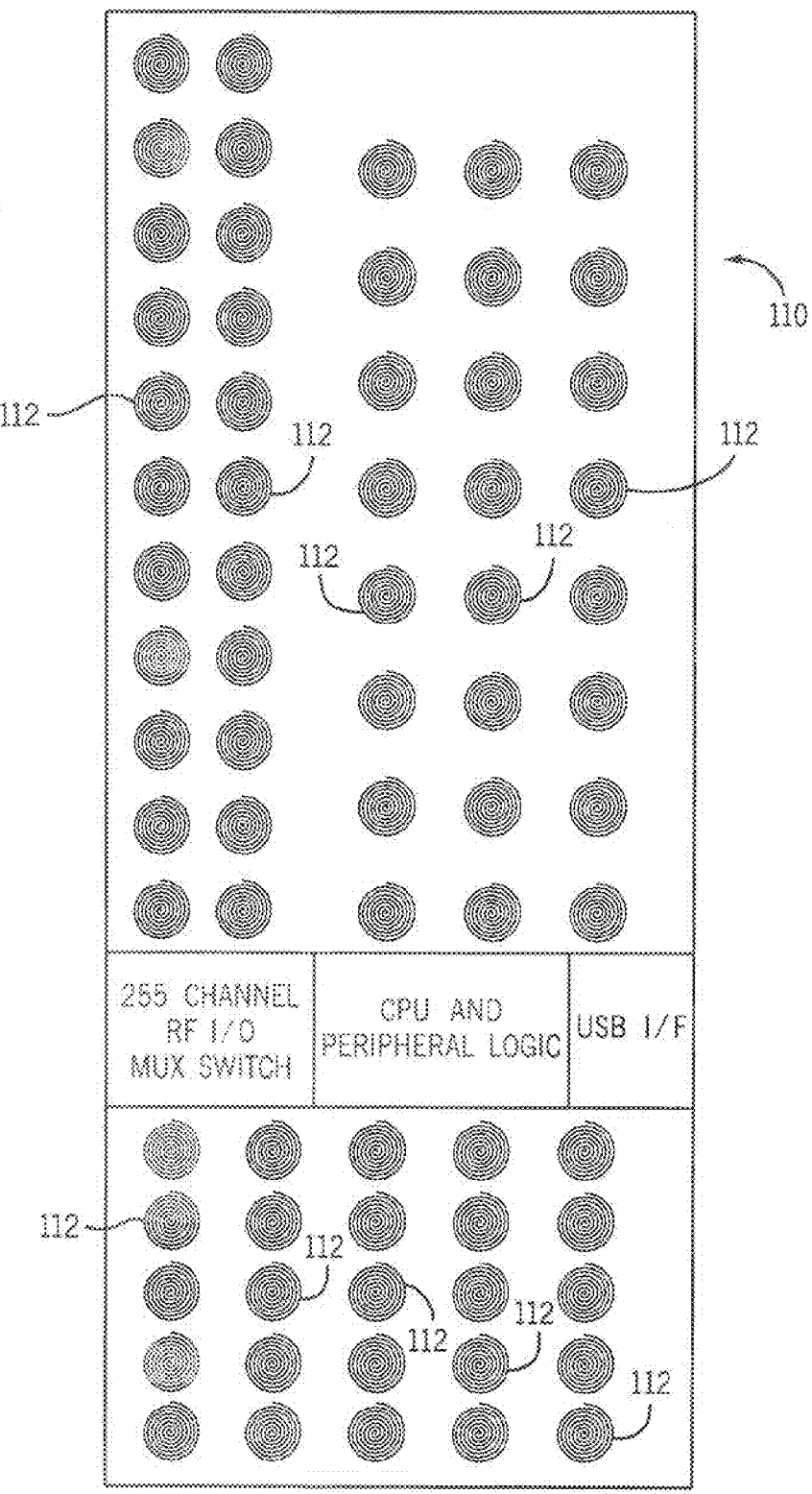
FIG. 5 is a top plan view of one embodiment of a printed circuit board having an array of radio frequency identification antennas. The printed circuit board shown in FIG. 5 can be used with the portion of the area of the system shown in FIG. 4.

FIGS. 1-3 illustrate various embodiments of reagent containers and sample containers. FIG. 5 illustrates a printed circuit board containing a plurality of antennas connected to a radio frequency identification reader. FIG. 1 illustrates where radio frequency identification tags can be attached to sample containers. Referring now to FIG. 1, a rack 10 has a plurality of slots 12 for holding sample containers 14, e.g., test tubes. Each slot 12 is separated from the adjacent slot by a resilient gripping device 16. Each resilient gripping device 16 comprises a tube gripper 16a and a tube gripper 16b. The resilient gripping devices 16 are positioned so that the gripper 16a of one gripping device 16 faces the gripper 16b of an adjacent gripping device 16. A sample container 14 is inserted between the gripper 16a of one gripping device 16 and the gripper 16b of an adjacent gripping device 16 to securely hold the sample container, i.e., test tube in an upright manner. Each resilient gripping device is typically constructed from a resilient material, such as, for example, resilient polymeric material. In FIG. 1, the sample container 14 is in the form of a tube. Each radio frequency identification tag 18 is attached at the lowermost end 14a of each sample container 14 and is read from underneath the container 14 by a radio frequency identification reader (not shown). The system should be able to identify and track a sample by radio frequency identification tag (constructed in accordance with ISO 18000 and either of ISO 14443 or ISO 15693) attached to the sample container. As mentioned earlier, radio frequency identification provides the ability to aggregate read information related to a sample in addition to the sample identifier. Information can include (a) demographics of a patient, (b) the date the sample was obtained, (c) the test(s) to be performed on the sample, (d) the type of sample, (e) the type of container, etc. Radio frequency identification can also be used to track shipping and storage conditions that may affect integrity of the sample. In addition, radio frequency identification can be used for writing information such as, for example, centrifugation performed on the sample, aspiration operations performed, potential contamination or dilution of a sample by material carried over by the tip of an aspirating device, freeze-thaw history of the sample, etc. Radio frequency identification also provides the ability to positively verify a sample identifier during aspiration or dispensing, thereby enabling an operator of the system to be given physical access to samples and reagents, except for those samples and reagents currently being aspirated or dispensed. Physical access to samples or reagents currently being aspirated or dispensed should be prohibited to the operator in order to ensure the safety of the operator.

FIG. 2 illustrates where radio frequency identification tags can be attached to reagent containers. Referring now to FIG. 2, a reagent container holder 20 holds a plurality of reagent containers 22, 24, and 26. In FIG. 2, the reagent container 22 is in the form of a cylindrical bottle having a flat bottom. The reagent container 22 can be used for reagents for clinical chemistry assays. The reagent containers 24 and 26 are in the form of cylindrical bottles having rounded bottoms. The reagent containers 24 and 26 can be used for reagents for immunoassays. The reagent container 26 is of lesser height than the reagent container 24. The lowermost end of container 22 is designated by the reference numeral 22a; the lowermost end of container 24 is designated by the reference numeral 24a; the lowermost end of container 26 is designated by the reference numeral 26a. Radio frequency identification tags 28a, 28b, and 28c are attached at the lowermost end 22a of container 22, the lowermost end 24a of container 24, and the lowermost end 26a of container 26, respectively, and are read from underneath the reagent containers 22, 24, and 26 by any radio frequency identification reader (not shown). In FIG. 2, the reagent containers 22, 24, and 26 are supported by and held by a sub-system comprising a locking, or adapter, plate 30, a base 32a, a holder comprising a lower portion 32b and an upper portion 32c, a vertical support 33 for supporting the upper portion 32c, a platform 34 upon which reagent containers can be mounted, at least one vertical support 35 for the platform 34, seats 36a, 36b, and 36c, and lifting handles 38. The seats 36a, 36b, and 36c are constructed so as to enable reagent containers for reagents for immunoassays to be securely, but removably, fastened to the platform 34 of the sub-system shown in FIG. 2. The lower portion 32b and the upper portion 32c of the holder have apertures (not shown) formed therein. These apertures are of such dimensions that a reagent container for reagents for clinical chemistry assays can be securely, but removably, inserted therein. The base 32a is an intermediate element that connects the platform 34 to the locking plate 30 via the at least one support 35. The lifting handles 38 have the function of providing a means for introducing and removing the sub-system holding the reagent containers from the storing and staging system shown in FIG. 4. The locking plate 30 has the function of securing the base 32a and the lower portion 32b of the holder to the storing and staging system shown in FIG. 4.

The system should be able to identify and track a reagent by radio frequency identification tag (constructed in accordance with ISO 18000 and either of ISO 14443 or ISO 15693 attached to the reagent container. As mentioned earlier, radio frequency identification provides the ability to aggregate read information related to the reagent in addition to the reagent identifier. Information can include calibration data, lot number of the reagent, serial number of the reagent, component identifier, assay identifier, expiration date of the reagent, kit size, package insert information, etc. Radio frequency identification can also be used to track shipping and storage conditions that may affect the integrity of the reagent. In addition, radio frequency identification can be used for writing information such as test count remaining, on-board expiration date (after the container has been opened), aspiration operations performed, potential contamination or dilution of a sample by material carried over by the tip of an aspirating device, etc. Radio frequency identification also provides the ability to positively verify a reagent identifier during aspiration or dispensing, thereby enabling an operator of the system to be given physical access to samples and reagents, except for those samples and reagents currently being aspirated or dispensed. Physical access to samples or reagents currently being aspirated or dispensed should be prohibited to the operator in order to ensure the safety of the operator.

Figure 7:
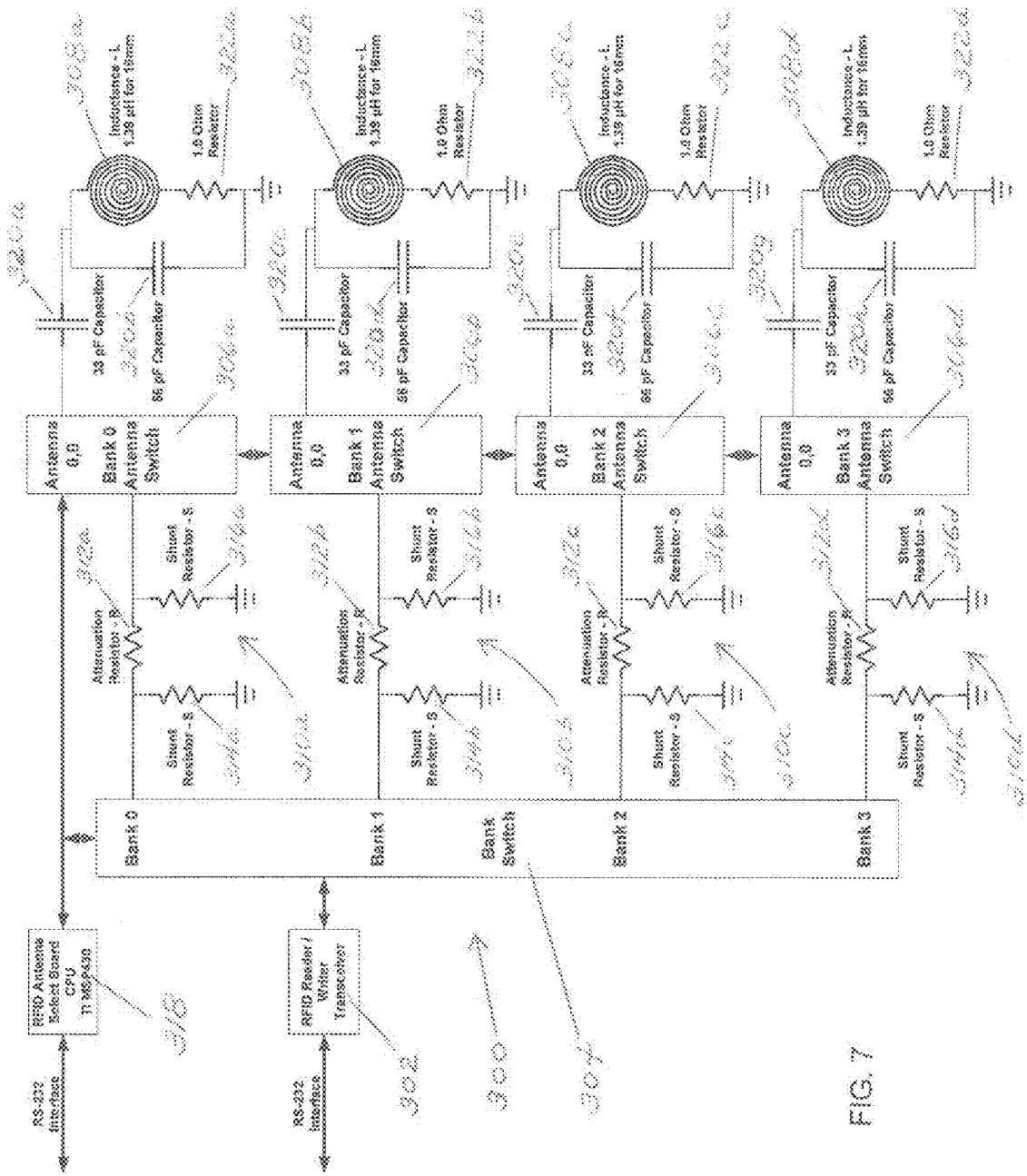
FIG. 7 is a circuit diagram illustrating circuits connecting a radio frequency identification reader/writer transceiver to antennas allocated in banks of antennas on a printed circuit board. Each bank circuit contains an attenuation component.

FIG. 3 illustrates attachment of radio frequency identification tags to microplates. Microplates are described in greater detail in U.S. Pat. No. 4,735,778 and in U.S. Patent Application Publication 2005/0242963, both of which are incorporated herein by reference. FIG. 7 of U.S. Patent Application Publication 2005/0242963 shows a microplate having a structure similar to that of the microplate 40 shown in FIG. 3 herein. A radio frequency identification tag 42, shown in phantom, is associated with the microplate 40. In FIG. 3, the microplate 40 has an upper portion 44 attached to a base 46. A plurality of wells 48 is formed in the upper portion 44 of the microplate 40. The upper portion 44 of the microplate 40 rests on the base 46. The radio frequency identification tag 42 is attached to the base 46. The radio frequency identification tag 42 is embedded within a portion of the microplate 40. In an alternative embodiment, the radio frequency identification tag can be applied to an exterior surface of the microplate. Any microplate having 8, 16, 24, 48, 96, 384, 768, 1536, etc., wells is contemplated for use in with the invention described herein. The radio frequency identification tag 42 can be read from underneath the microplate 40. Alternatively, the radio frequency identification tag 42 can be read from the side of the microplate 40 if the orientation of the radio frequency identification tag is changed to make such an alternative viable. Because the distance between the radio frequency identification reader and radio frequency identification tag is small, the placement of the radio frequency identification tag 42 also indicates the physical orientation of the microplate 40. For example, if the radio frequency identification tag 42 is always located adjacent to the A1 position on the microplate 40, reading the radio frequency identification tag 42 ensures that the microplate 40 is oriented with position A1 over the radio frequency identification reader (i.e., the position at the upper left hand corner of the microplate). The system should be able to identify and track a microplate by the radio frequency identification tag (as constructed in accordance with ISO 18000 and either of ISO 14443 or ISO 15693) on the microplate. Radio frequency identification provides the ability to aggregate read information related to the assay steps, such as, for example, loading, dispensing, and the reagents in the microplate, in addition to the microplate identifier. Information can include lot number of the microplate, serial number of the microplate, expiration date of the microplate, etc. Radio frequency identification can also be used to track shipping and storage conditions that may affect integrity of the microplate. In addition, radio frequency identification can be used for writing information to a radio frequency identification tag, such as, for example, date used, on-board expiration date (after the container has been opened), the time at which samples and reagents are dispensed into a microplate, the time at which a microplate is subjected to incubation, the time at which the reactions in a microplate are read by a reader, etc.

Figure 4:
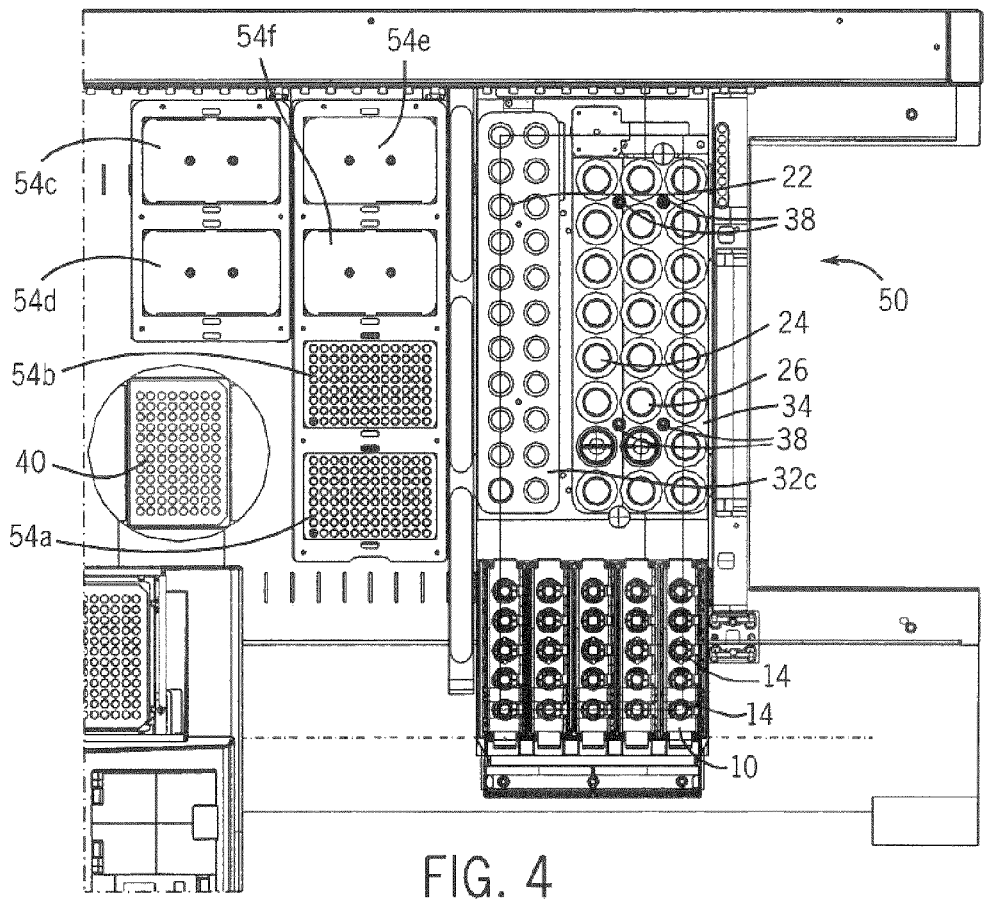
FIG. 4 is a top plan view of a portion of an area of a system for storing and staging sample containers of the type shown in FIG. 1, reagent containers of the type shown in FIG. 2, and microplates of the type shown in FIG. 3.

FIG. 4 illustrates a storage area/staging area 50 for reagents, samples, and other supplies. The storage area/staging area 50 provides positions for the sample containers shown in FIG. 1, the reagent containers shown in FIG. 2, and the microplates shown in FIG. 3. A microplate 40 is shown in position at the left side of the view of the storage area/staging area 50. Reagent containers 22 containing reagents for clinical chemistry assays are positioned in the apertures (not shown) in upper portion 32c and lower portion 32b of the holder, as illustrated in greater detail in FIG. 2. The reagent containers 24 and 26 containing reagents for immunoassays are positioned in the seats 36c and 36b, respectively, as illustrated in greater detail in FIG. 2. Sample containers 14 containing biological samples are positioned in the slots 12 of the rack 10, as illustrated in greater detail in FIG. 1. Disposable tip holders 54a and 54b are located adjacent to the microplate 52. Additional locations for disposable tip holders are designated at 54c, 54d, 54e, and 54f. The radio frequency identification tags can be read at various positions beneath the storage area 50.

In FIG. 5, a printed circuit board 110 contains a plurality of antennas 112 connected to a radio frequency identification reader. Each antenna 112 is selectively activated by means of electronics. In FIG. 5, the 5×5 array of antennas at the lower portion of the printed circuit board 110 corresponds to the portion of the storage area/staging area 50 of FIG. 4 where the sample containers 14 are located. The 3×8 array of antennas at the upper right portion of the printed circuit board 110 corresponds to the portion of the storage area/staging area 50 of FIG. 4 where the reagent containers 24 and 26 containing reagents for immunoassays are located. The 2×11 array of antennas at the upper left portion of the printed circuit board 110 corresponds to the portion of the storage area/staging area 50 of FIG. 4 where the reagent containers 22 containing reagents for clinical chemistry assays are located. A large printed circuit board containing a plurality of antennas, such as that shown in FIG. 5, eliminates the need to move a reader head. Through the use of a large printed circuit board containing a plurality of antennas, such as that shown in FIG. 5, signals can be transmitted from antennas 112 connected to the radio frequency identification reader to a radio frequency identification tag. Similarly, signals transmitted from the radio frequency identification tags attached to containers can be received by antennas 112 for further processing by a radio frequency identification reader connected to the antennas 112. It is also within the scope of this invention to employ a plurality of radio frequency identification readers with a printed circuit board of the type shown in FIG. 5. It should be noted that a printed circuit board is not required to support the antennas. For example, the antennas can be positioned in any manner so long as radio frequency signals can be transmitted from the antennas and received by the antennas and the radio frequency signals received by the antennas can be read by a radio frequency identification reader.

In order for signals to be transmitted between an antenna of a radio frequency identification tag and an antenna connected to a radio frequency identification reader, there must be an antenna aperture between the antenna of the radio frequency identification tag and the antenna connected to the radio frequency identification reader. Referring now to FIG. 2, the bearings (not shown), the dispersion spindle, which is designated by the reference numeral 120 in FIG. 2, and the gear for rotating the dispersion spindle, which is designated by the reference numeral 122 in FIG. 2, should be transparent to the signals transmitted between the antenna of a radio frequency identification tag and an antenna connected to the radio frequency identification reader. The bearings, the dispersion spindle, and the gear are preferably made from a polymeric material. The materials of the barrier that is not in the path of the signals transmitted between the antenna of a radio frequency identification tag and an antenna connected to the radio frequency identification reader can be formed from a metallic material or carbon impregnated plastic. This barrier is designated by the reference numerals 32a and 34 of FIG. 2. By the use of appropriate materials, antenna apertures can be constructed to provide adequate sensitivity as well as selectivity. After a prototype printed circuit board containing a plurality of antennas has been completed, testing may indicate that additional shaping techniques for antenna apertures should be employed. Additional metal, or other materials exhibiting metal-like properties, can be employed in various geometric shapes to enhance selectivity and propagation of radio frequency waves. It is expected that as new techniques become available to reduce cost of radio frequency identification tags, such techniques will be employed.

Smaller radio frequency identification antennas can be used to decrease reading range, increase selectivity, and provide physical orientation performance, but such antennas require closer proximity of the radio frequency identification tag to the radio frequency identification reader.

TABLE III shows values used for the different antenna sizes for antennas attached to a printed circuit board:

TABLE III

| Diameter (mm) | Inductance (μH) | Capacitance (pF) |
|---|---|---|
| 26 | 2.31 | 63 |
| 20 | 1.68 | 82 |
| 16 | 1.39 | 89 |
| 12 | 1.54 | 87 |

Antennas having the parameters shown in TABLE III provide resonance coupling of antennas that enable radio frequency identification tags and radio frequency identification readers to exchange information while in a near field relationship. The benefit of a near field relationship is improvement in selectivity.

Attenuation of the power of the radio frequency identification reader also improves selectivity. In other words, by reducing the magnitude of the radio frequency identification signal, the number of antennas that can receive the signal is also reduced, preferably to a single antenna. It would be ideal to have the radio frequency identification signal attenuated to such a degree that only a very small number of antennas could even receive any fraction of the signal. Attenuation can be achieved physically or electrically. By inserting an attenuation component into the circuit of the radio frequency reader, such as, for example, by the insertion of a resistor in the circuit of the radio frequency reader, the distance at which a signal is capable of being received can be minimized. By adding attenuation material (metal or carbon impregnated resin) around an antenna, the antenna can be partially shielded, thereby shaping the field thereof. The shielding provided by carbon impregnated resin or metal blocks radio frequency energy. In fact, the distance at which a signal can be read can be reduced and directed so that at least 75% of a radio frequency identification tag needs to be directly in register with the antenna connected to a radio frequency identification reader to enable an exchange of data to occur. Attenuation of the power of the radio frequency identification reader thereby provides the ultimate solution for near field selectivity, because, at any given time, attenuation can ensure that only one antenna can receive a signal from a given radio frequency identification tag. In the following table, three positions of radio frequency identification tags are shown: immunoassay bottle (i.e., a bottle containing a reagent for an immunoassay), clinical chemistry bottle (i.e., a bottle containing a reagent for a clinical chemistry assay), and sample tube (i.e., a container for a sample). The read distances differ for each location. TABLE IV shows the distances between the printed circuit board supporting the antennas and the radio frequency identification tag attached to a container.

TABLE IV

| Container | Read distance (inches) |
|---|---|
| Immunoassay bottle | 1.45 |
| Clinical chemistry bottle | 0.48 |
| Sample tube | ~0.00 (printed circuit board is coated with paint for sealing out humidity, having a thickness on the order of 0.002 inch) |

The selectivity and attenuation requirements are different for each location. To accommodate these variations, "banks" of antennas are used, such that each bank of antennas has its own level of attenuation. As used herein, the term "bank" means an area containing a group of antennas, wherein attenuation of a radio frequency signal enables a specified level of power to be transmitted to that group of antennas only and to no other group of antennas. Each individual antenna in a given group of antennas would experience the same degree of attenuation of a radio frequency signal. Banks are selected to recognize physical phenomena, such as, for example, distance from an antenna to a radio frequency identification tag, obstacles such as metal components, such as, for example, metal bearings. For example, in order to read a radio frequency identification tag in the vicinity of a metal bearing requires significantly more power, i.e., less attenuation, than would reading a radio frequency identification tag that is not partially blocked by a metal bearing. An excessive quantity of power is not desirable, because such excessive quantity would enable signals from a single antenna to be received by a plurality of radio frequency identification tags. An insufficient quantity of power is also not desirable, because such insufficient quantity would prevent reading a radio frequency identification tag or would lead to an unreliable reading of a radio frequency identification tag.

Figure 6:
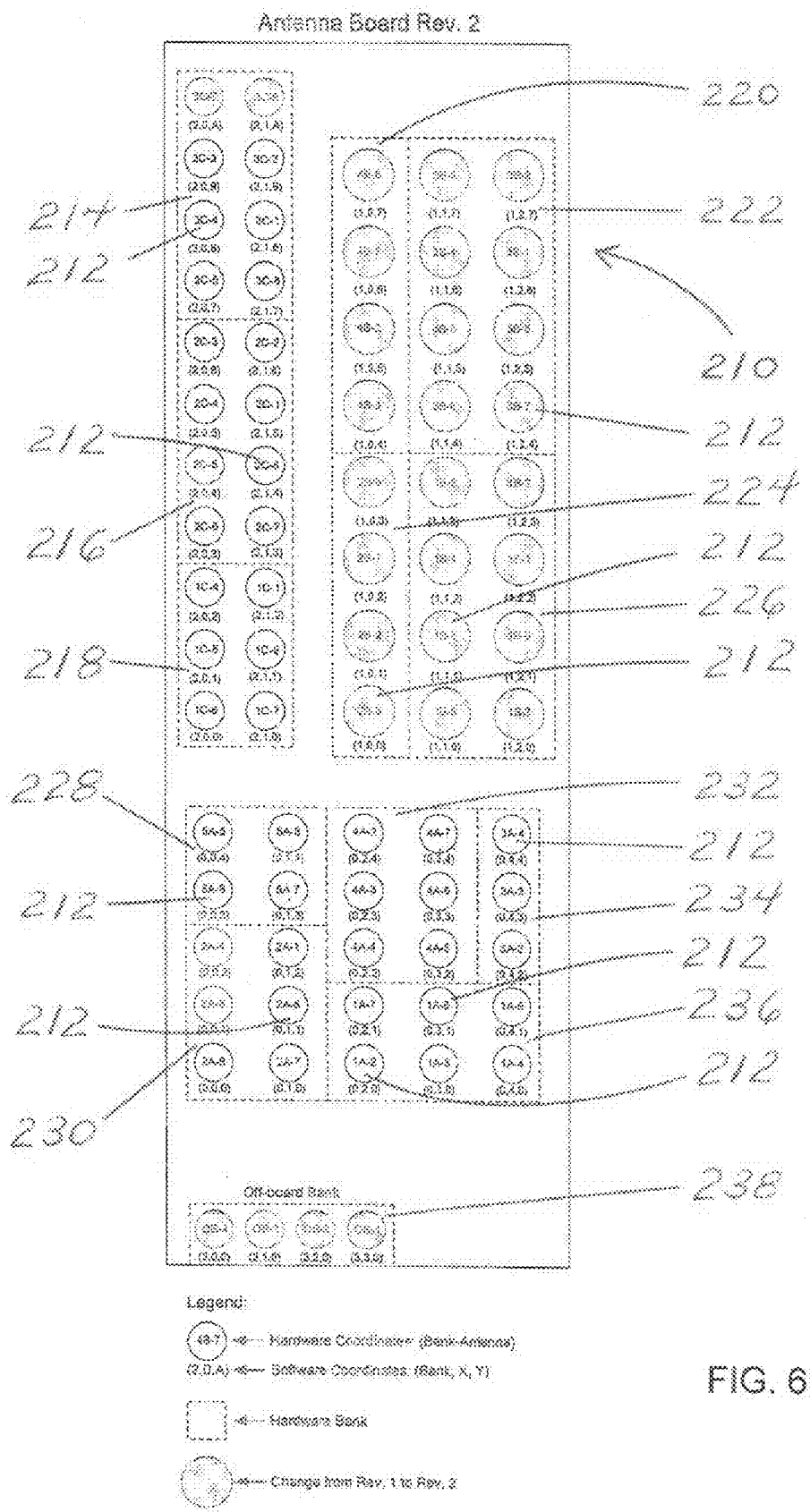
FIG. 6 is a top plan view of another embodiment of a printed circuit board having an array of radio frequency identification antennas. The printed circuit board shown in FIG. 6 can be used with the portion of the area of the system shown in FIG. 4.

Referring now to FIG. 6, a printed circuit board 210 contains a plurality of radio frequency antennas 212. Each antenna 212 is selectively activated by means of electronics. The antennas 212 are positioned in a plurality of on-board banks 214, 216, 218, 220, 222, 224, 226, 228, 230, 232, 234, and 236 and a single off-board bank 238. Additional off-board antennas or banks of antennas or both antennas and banks of antennas can be used, if so desired. In FIG. 6, the 5×5 array of antennas at the lower portion of the printed circuit board 210 corresponds to the portion of the storage area/staging area 50 of FIG. 4 where the sample containers 14 are located. The 3×8 array of antennas at the upper right portion of the printed circuit board 210 corresponds to the portion of the storage area/staging area 50 of FIG. 4 where the reagent containers 24 and 26 containing reagents for immunoassays are located. The 2×11 array of antennas at the upper left portion of the printed circuit board 210 corresponds to the portion of the storage area/staging area 50 of FIG. 4 where the reagent containers 22 containing reagents for clinical chemistry assays are located. A large printed circuit board containing a plurality of antennas, such as that shown in FIG. 6, eliminates the need to move a reader head. Through the use of a large printed circuit board containing a plurality of antennas, such as that shown in FIG. 6, signals from the radio frequency identification tags attached to containers can be read by stationary antennas 212 for further processing by a radio frequency identification reader connected to the antennas 212. It is also within the scope of this invention to employ a plurality of radio frequency identification readers with a printed circuit board of the type shown in FIG. 6. The arrangement of antennas illustrated in FIG. 6 does not differ from the arrangement of antennas in FIG. 6. However, by means of the use of on-board banks 214, 216, 218, 220, 222, 224, 226, 228, 230, 232, 234, and 236 and a single off-board bank 238, variation of attenuation can be employed to compensate for physical differences between antennas and radio frequency identification tags. In a given bank, a signal read by one antenna can be isolated from the other antennas in that bank by an appropriate level of attenuation. In FIG. 6, each antenna is marked with hardware coordinates in which the number of the bank is followed by the number of the antenna in that bank; each antenna is also marked with software coordinates in which the number of the bank and Cartesian coordinates (X,Y) are designated. Also in FIG. 6, each bank is bounded by dashed lines.

In addition to distance between the radio frequency identification tag and the antenna, another important feature of the path between the radio frequency identification reader and the radio frequency identification tag exists. This feature involves obstruction by means of metallic components, such as, for example bearings. As previously described with respect to the printed circuit board illustrated in FIG. 5, in order for signals to be transmitted between the antenna of a radio frequency identification tag and an antenna connected to a radio frequency identification reader, there must be an antenna aperture between the antenna of the radio frequency identification tag and the antenna connected to the radio frequency identification reader. Referring now to FIG. 2, the bearings (not shown), the dispersion spindle, which is designated by the reference numeral 120 in FIG. 2, and the gear for rotating the dispersion spindle, which is designated by the reference numeral 122 in FIG. 2, should be transparent to the signals transmitted between the antenna of a radio frequency identification tag and an antenna connected to the radio frequency identification reader. The bearings, the dispersion spindle, and the gear are preferably made from a polymeric material. The materials of the barrier that is not in the path of the signals transmitted between the antenna of a radio frequency identification tag and an antenna connected to the radio frequency identification reader can be formed from a metallic material or carbon impregnated plastic. This barrier is designated by the reference numerals 32a and 34 of FIG. 2. By the use of appropriate materials, antenna apertures can be constructed to provide adequate sensitivity as well as selectivity. After a prototype printed circuit board containing a plurality of antennas has been completed, testing may indicate that additional shaping techniques for antenna apertures should be employed. Additional metal, or other materials exhibiting metal-like properties, can be employed in various geometric shapes to enhance selectivity and propagation of radio frequency waves. It is expected that as new techniques become available to reduce cost of radio frequency identification tags, such techniques will be employed.

Smaller radio frequency identification antennas can be used to decrease reading range, increase selectivity, and provide physical orientation performance, but such antennas require closer proximity of the radio frequency identification tag to the radio frequency identification reader.

There is a separate radio frequency circuit for each bank, and an attenuator can be inserted into that circuit. Each bank can be attenuated differently, thereby rendering it possible to tune antennas for different physical situations. Attenuators that are suitable for use herein are described in Attenuators—Microwave Encyclopedia—Microwaves101.com, available at the website http://www.microwaves101.com/encyclopedia/attenuators.cfm and at Attenuators dissipation—Microwave Encyclopedia—Microwaves101.com, available at the website http://www.microwaves101.com/encyclopedia/attenuatordiss.cfm, both of which are incorporated herein by reference. FIG. 7 illustrates a circuit 300 that uses pi attenuators for attenuating radio frequency signals. In FIG. 7, a radio frequency identification reader/writer transceiver 302 is connected to a bank switch 304 for Bank 0, Bank 1, Bank 2, and Bank 3. The bank switch 304 is connected to an antenna switch 306a for Bank 0, an antenna switch 306b for Bank 1, an antenna switch 306c for Bank 2, and an antenna switch 306d for Bank 3. The bank switch 304 and the antenna switches 306a, 306b, 306c, and 306d are associated with a printed circuit board (not shown). Radio frequency antennas 308a, 308b, 308c, and 308d are located at position 0,0 in Bank 0, Bank 1, Bank 2, and Bank 3, respectively, on the printed circuit board. Pi attenuators 310a, 310b, 310c, and 310d are positioned in the circuits between the bank switch 304 and the antenna switches 306a, 306b, 306c, and 306d. Each pi attenuator 310a, 310b, 310c, and 310d includes a series resistor 312a, 312b, 312c, and 312d, respectively, a first shunt resistor 314a, 314b, 314c, and 314d, respectively, and a second shunt resistor 316a, 316b, 316c, and 316d, respectively. The bank switch 304 and the antenna switches 306a, 306b, 306c, and 306d are connected to a radio frequency identification antenna select board central processing unit 318. FIG. 7 also shows various capacitors 320a, 320b, 320c, 320d, 320e, 320f, 320g, and 320h and various resistors 322a, 322b, 322c, and 322d in the circuit 300. Selection of and positioning of the capacitors 320a, 320b, 320c, 320d, 320e, 320f, 320g, and 320h and resistors 322a, 322b, 322c, and 322d in the circuit 300 can be easily determined by one of ordinary skill in the art.

In order to read a signal from a radio frequency identification tag (not shown) attached to a container (not shown), the container is positioned adjacent to a radio frequency antenna 308a, 308b, 308c, 308d so that the radio frequency identification tag is in sufficiently close proximity to the radio frequency antenna 308a, 308b, 308c, 308d that the signal is capable of being received by the radio frequency identification antenna 308a, 308b, 308c, 308d. When both the bank switch 304 and the appropriate antenna switch 306a, 306b, 306c, or 306d for the appropriate radio frequency antenna 308a, 308b, 308c, or 308d are closed, the signal from the radio frequency identification tag attached to the container can be received by the appropriate radio frequency antenna 308a, 308b, 308c, or 308d and the signal thus received can be read by the radio frequency identification reader/writer transceiver 302. It should be noted that types of attenuators other than pi attenuators could be used.

TABLE V shows the amount of attenuation used for each bank for generating the smallest signal that can successfully provide a reading for each radio frequency identification tag in register with a specific antenna, while maximizing the selectivity of the antenna so that no radio frequency identification tag can be read by more than one antenna. It should be noted that at least 75% of the area of a radio frequency identification tag is required to be in register with an antenna in order for a reading of the radio frequency identification tag to be successful.

TABLE V

| Container | Bank | Attenuation (dB) | Shunt resistor (ohms) | Series resistor (ohms) |
| --- | --- | --- | --- | --- |
| Sample tube | 0 | −8 | 115 | 52.3 |
| Immunoassay bottle | 1 | 0 | Not installed | 0 |
| Clinical chemistry bottle | 2 | −15 | 71.5 | 137 |

It should be noted that it is relatively simple for one of ordinary skill in the art to determine resistance values for shunt resistors and series resistors for various types of attenuators in order to derive the desired level of attenuation. It is expected that an attenuation range of from about 0 dB to about −30 dB is suitable for use with the apparatus and method described herein. However, a greater level of attenuation, i.e., a value lower than −30 dB can be used, if desired.

By experimentation, the actual dimensions were optimized, inductances of antennas were measured, and capacitance values were determined. Some tuning is required, because not all values match the theoretical model precisely, on account of placement of components, inductance and capacitance of the trace (i.e., conductor) on the printed circuit board, etc.

Column 0 of Bank 1 contains metal bearings in the path between the radio frequency identification reader and the radio frequency identification tags. These metal bearings to block significant amounts of radio frequency energy. In contrast, Columns 1 and 2 of Bank 0 have holes beneath radio frequency identification tags that are transparent to radio frequency energy. In order to compensate and maintain selectivity, Column 0 of Bank 1 will have different attenuation than do Columns 1 and 2 of Bank 1. TABLE VI shows that further subdivision of a given bank can be useful when different degrees of attenuation are required within the given bank.

TABLE VI

| Container | Bank | Column in bank | Attenuation (dB) | Shunt resistor (ohms) | Series resistor (ohms) |
| --- | --- | --- | --- | --- | --- |
| Sample tube | 0 | | −8 | 115 | 52.3 |
| Immunoassay bottle | 1 | 0 | 0 | Not installed | 0 |
| Immunoassay bottle | 1 | 1, 2 | −12 | 82.5 | 93.1 |
| Clinical chemistry bottle | 2 | | −15 | 71.5 | 137 |

It should be noted that it is relatively simple for one of ordinary skill in the art to determine resistance values for shunt resistors and series resistors for various types of attenuators in order to derive the desired level of attenuation.

Another technique that improves selectivity is the judicious selection of the dimensions of the antenna (i.e., diameter in the case of circular antennas). As described earlier, a variety of antennas were tested, 26 mm, 20 mm, 16 mm, and 12 mm. Signals from radio frequency identification tags, circular in shape and having different diameters (8 mm, 12 mm, 25 mm), were received by means of these antennas, and many showed comparable performance (i.e., read distance as a function of attenuation). However, the antennas having larger diameters could receive signals from radio frequency identification tags over a larger area, and consequently, decreased relative selectivity, given that the separation between the container and the radio frequency identification tag was fixed. In addition, the antennas having smaller diameters were not able to receive the signals from the radio frequency identification tags around the metal bearings in Column 0 of Bank 1, because the radio frequency field was too narrow and was completely occluded by the metal bearings. Thus, a compromise was reached; 16 mm antennas were chosen for all locations. Smaller antennas could have been chosen for the columns not associated with bearings, but simplicity and commonality of design were also criteria. In general, the smallest antennas (12 mm diameter) demonstrated the best selectivity.

Figures 8A, 8B:
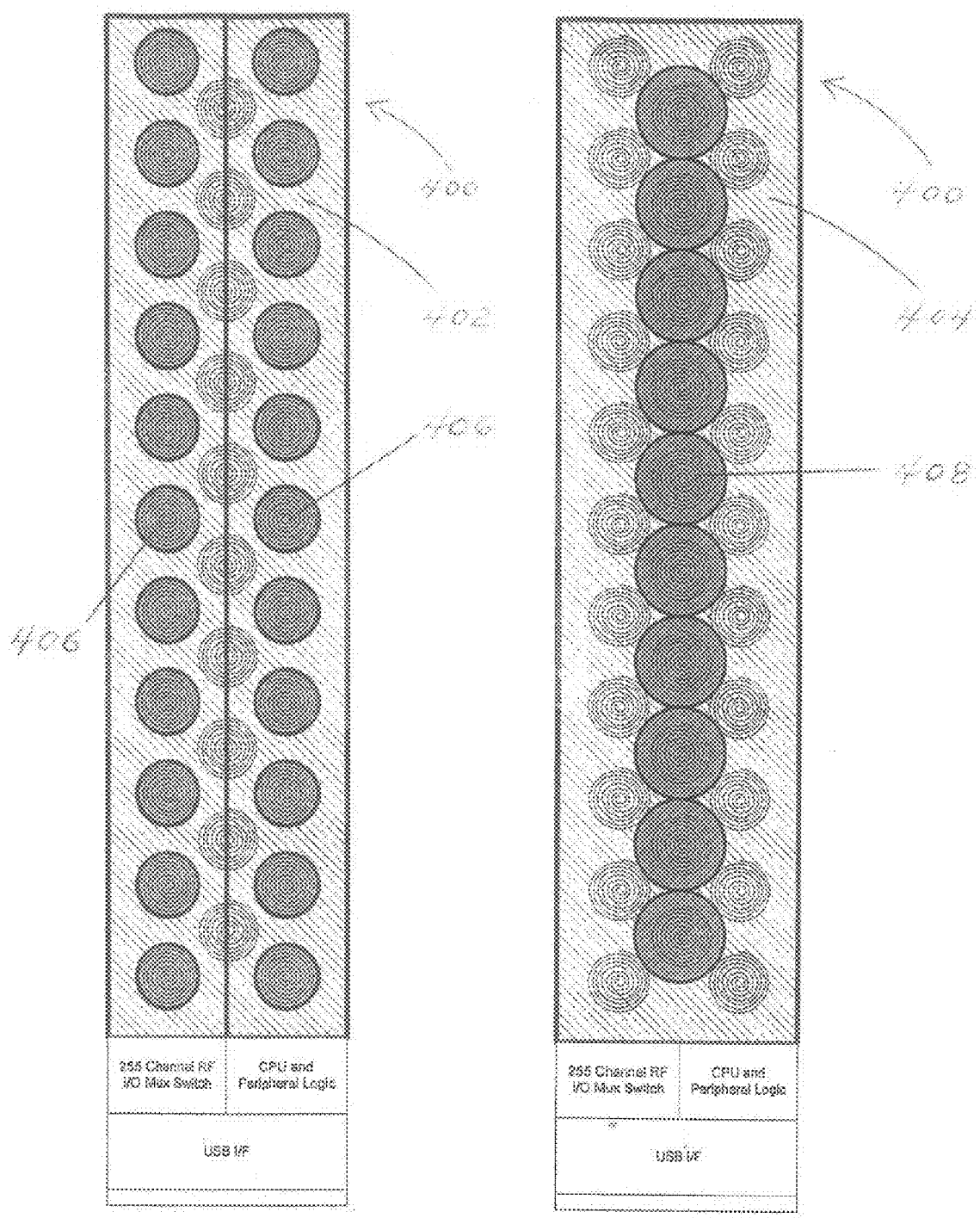
FIG. 8A is a top plan view of a multi-layered printed circuit board supporting a plurality of antennas connected to a radio frequency identification reader. The top layer comprises two columns of antennas. The bottom layer comprises one column of antennas.
FIG. 8B is a top plan view of a multi-layered printed circuit board supporting a plurality of antennas connected to a radio frequency identification reader. The top layer comprises two columns of antennas. The bottom layer comprises one column of antennas.

The use of multi-layered printed circuit boards and information specific top radio frequency identification tags improves selectivity and also provides flexibility in reading location. A multi-layered printed circuit board is a printed circuit board that has a plurality of layers of conducting material and a plurality of layers of insulating material, a layer of insulating material separating two layers of conducting material. A common loading area for sample tubes and reagent bottles is often desirable. A common loading area is often more efficient than separate loading areas for sample tubes and reagent bottles. In FIGS. 8A and 8B, a two-column set of antennas for receiving signals from radio frequency identification tags is overlaid with a one-column set of antennas to form a multi-layered printed circuit board 400. The top layer 402 is configured to read radio frequency identification tags on two narrow sample tube racks (not shown), which have a single width of about one inch. The bottom layer 404 is configured to read radio frequency identification tags on one wide reagent bottle rack (not shown), which has a double width of about two inches. The antennas in the top layer 402 are designated by the reference numeral 406. The antennas in the bottom layer 404 are designated by the reference numeral 408. Although there is some overlap of the circuitry, traces, and antennas 406, 408 of the top layer 402 and the bottom layer 404 of the multi-layered printed circuit board 400, specific information related to the radio frequency identification tag can be used to select the proper column of antennas. For example, if the radio frequency identification tag of a sample tube were detected, then the top layer 402 of two narrow columns of antennas 406 would be selected. If the radio frequency identification tag of a reagent bottle were detected, then the bottom layer 404 of one wide column of antennas 408 would be selected. If both types of radio frequency identification tags were detected, then an error would be declared and the assistance of an operator would be requested.

According to the system described herein, radio frequency identification tags can be selectively read at each position of a reagent container or at each position of a sample container, e.g., a sample tube, from a point below the reagent container or sample container. Because the distance of the radio frequency identification tag from the radio frequency identification reader is typically small, e.g., less than 1 inch, and the antenna aperture limits side lobes, the placement of the radio frequency identification tag on the container can also provide information relating to the type of analyzer, e.g., clinical chemistry analyzer, immunoassay analyzer, and the type of container, e.g., sample container, reagent container, thereby providing (a) improved functioning of automated analyzer(s) in a system, (b) improved chain of custody, i.e., improved information relating to locations occupied by a given container in the present and at times previous to the present, and (c) improved safety to patients by ensuring accurate results of assays.

The radio frequency identification antennas provide a solution to the problem resulting from near field selectivity, because only one antenna can receive a signal from any given tag at any given time. In addition, by using information specific to a given tag, for sample tubes and reagent bottles, common, multiple-layer antennas can be used to simplify apparatus/operator interfaces and utilize limited areas efficiently.

The arrangement described herein can be used with any radio frequency identification tag and any radio frequency identification reader interface. By ensuring that the radio frequency identification tag can only be read and written to in a single location, geometric location and orientation can be verified. The benefit of this feature is that radio frequency identification tags attached to containers holding samples, reagents, or other commodities can be read at the point of dispensing, incubating, or other processing step, and there is no opportunity to exchange samples, reagents, and other commodities after such a read. The arrangement described herein extends the use of radio frequency identification technology, by providing means for improving selectivity, positive identification of samples, reagents, and other commodities. Moreover, transfer of data can be carried out at a precise geometric location or a precise orientation of radio frequency identification tag or both a precise geometric location and a precise orientation of radio frequency identification tag.

Multiple-layering of antennas can be extended to different frequencies or read protocols or both. By selectively energizing each antenna layer, data specific to a given radio frequency identification tag can be searched for, in order to determine which antennas, frequencies, protocols, or any combination of the foregoing can be used. This versatility enables the use of different types of radio frequency identification tags, enables the detection of errors, and enables selection of particular types of radio frequency identification tags and the ignoring of others.

Operation

Radio frequency identification tags can be either attached to or molded into a container, such as, for example, a reagent container, a sample container, e.g., a sample tube, a microplate, and the like. Initial manufacturing information is typically programmed into radio frequency identification tags. Storage and shipping information (e.g., logistics) are typically concatenated to previous data in radio frequency identification tags.

Radio frequency identification tags on reagent containers, sample containers, and microplates, and the like, are read when placed on the radio frequency identification system of this invention. A plurality of antennas connected to a radio frequency identification reader is used in lieu of a movable radio frequency identification reader. One or more antennas connected to the radio frequency identification reader can be selected, and then information in the radio frequency identification tags of the containers can be read. Information and physical locations of reagent containers, sample containers, and the like, can be substantiated.

As the contents of the reagent containers, sample containers, microplates, etc. are accessed and the contents are consumed during the performance of an assay, additional information can be concatenated to previous data in radio frequency identification tags. A large printed circuit board containing a plurality of antennas, such as the type shown in FIGS. 5, 6, 7, 8A, and 8B, eliminates the need to move an antenna.

The power of the radio frequency identification reader is limited to 4 watts EIRP. In the systems described herein, the planes of the antennas connected to the radio frequency identification reader and the antennas of the radio frequency identification tags on a single printed circuit board are preferably parallel to each other, and, when being read, the center of each radio frequency identification tag antenna is preferably positioned over the center of the antenna connected to the radio frequency identification reader. The distance from the antenna connected to the radio frequency identification reader to the antenna of the radio frequency identification tag typically ranges from about 0.100 inch to about 1.25 inches.

Radio frequency identification can be used to enhance information on the containers for reagents, containers for samples, microplates, and the like, so that the information can be directly linked to a database and provide (a) improved functioning of automated analyzer(s) in a system, (b) improved chain of custody, i.e., improved information relating to locations occupied by a given container in the present and at times previous to the present, and (c) improved safety to patients by ensuring accurate results of assays. This information includes, but is not limited to, information related to the automated analyzer, information related to the environments experienced during shipping, storage, and usage of the contents of the containers, and information related to the containers. For example, the system described herein can be used to compare the storage information of a sample in a sample container or of a reagent in a reagent container to a set of acceptable storage conditions, thereby facilitating the rejection or acceptance of the sample in the sample container for analysis of the sample or the rejection or acceptance of the reagent in the reagent container for performance of an assay, based on the aforementioned comparison function performed.

Because radio frequency identification tags can be read and written to at a processing location (i.e., an aspiration location, a dispensing location, etc.), physical access for an operator to samples and reagents, except for those samples and reagents currently being aspirated or dispensed, can be increased. However, physical access to samples or reagents currently being aspirated or dispensed should be prohibited to the operator in order to ensure the safety of the operator.

Automated analyzers that can be used with the radio frequency identification system of this invention include, but are not limited to, automated immunoassay instruments, automated clinical chemistry instruments, automated hematology instruments, automated nucleic acid analyzer instruments, such as, for example, automated nucleic acid microarray analyzer instruments and an automated nucleic acid amplification analyzer instrument, automated slide processing instruments, and automated protein analyzer instruments. Of course, the aforementioned instruments will include the subsystems required to enable operation thereof, such as, for example, immunoassay readers, clinical chemistry readers, software, fluid transfer mechanisms, etc. The automated analyzers that can be used with the radio frequency identification instruments can further include an automated sample processing station, such as, for example, an apparatus for extraction of nucleic acid from a biological sample. It is also possible for the system of this invention to have a plurality of analysis stations, wherein each of the plurality of analysis stations comprises apparatus for the automated analysis of a biological sample. The analysis stations can employ analyzers from list of analyzers mentioned previously. In addition, in certain embodiments the system of this invention can further comprise an automated sample processing station.

Various modifications and alterations of this invention will become apparent to those skilled in the art without departing from the scope and spirit of this invention, and it should be understood that this invention is not to be unduly limited to the illustrative embodiments set forth herein.

What is claimed is:

1. A system comprising a plurality of containers, each of which has a radio frequency identification tag attached thereto at a suitable position thereon, the system further including at least one radio frequency identification reader, said at least one radio frequency identification reader capable of reading signals from a plurality of antennas, said plurality of antennas disposed in a plurality of banks of antennas, each bank of antennas capable of being attenuated at a different power level, whereby physical differences in between antennas and radio frequency identification tags can be compensated for.

2. The system of claim 1, wherein at least 75% of the area of the radio frequency identification tag must be in register with an antenna in order to be read successfully.

3. The system of claim 1, wherein the location of a radio frequency identification tag is determined from the antenna receiving a signal from the radio frequency identification tag.

4. The system of claim 1, wherein a single radio frequency identification reader is activated at any one time.

5. The system of claim 1, wherein the relationship between the radio frequency identification tag and the radio frequency identification reader relationship is based on distance between the radio frequency identification tag and the antenna.

6. The system of claim 1, wherein the relationship between the radio frequency identification tag and the radio frequency identification reader is based on obstacles between the radio frequency identification tag and the antenna.

7. The system of claim 1, wherein attenuation can range from about 0 to about −30 dB.

8. The system of claim 1, wherein the system comprises at least one analysis station comprising an automated immunoassay instrument.

9. The system of claim 1, wherein the at least one analysis station comprises an automated clinical chemistry instrument.

10. The system of claim 1, wherein the at least one analysis station comprises an automated hematology instrument.

11. The system of claim 1, wherein the at least one analysis station comprises an automated nucleic acid analyzer instrument.

12. The system of claim 11, wherein the automated nucleic acid analyzer instrument is selected from the group consisting of an automated nucleic acid microarray analyzer instrument and an automated nucleic acid amplification analyzer instrument.

13. The system of claim 1, wherein the at least one analysis station comprises an automated slide processing instrument.

14. The system of claim 1, wherein the at least one analysis station comprises an automated protein analyzer instrument.

15. The system of claim 1, further comprising an automated sample processing station.

16. The system of claim 15, wherein the automated sample processing station comprises apparatus for extraction of nucleic acid from a biological sample.

17. The system of claim 1, comprising a plurality of analysis stations, wherein each of said plurality of analysis stations comprises apparatus for the automated analysis of a biological sample.

18. The system of claim 17, comprising at least two analysis stations, wherein said at least two analysis stations are selected from the group consisting of automated immunoassay instruments, automated hematology instruments, automated nucleic acid analyzer instruments, automated slide processing instruments, and automated protein analyzer instruments.

19. The system of claim 18, further comprising an automated sample processing station.

20. The system of claim 1, wherein each of the plurality of containers is capable of being moved to a position proximate to one of the plurality of antennas, whereby the amount of noise and interference from nearby radio frequency identification tags on other containers are insufficient to adversely affect the integrity of the data received by the antenna connected to the radio frequency identification reader.

21. The system of claim 1, wherein each of said plurality of stationary antennas connected to said radio frequency identification reader is a trace on a printed circuit board.

22. The system of claim 1, wherein each of said plurality of stationary antennas connected to said radio frequency identification reader is not a trace on a printed circuit board.

23. The system of claim 1, wherein the radio frequency identification tags are positioned at the lowermost portions of the containers.

24. The system of claim 1, wherein the radio frequency identification tags are encapsulated.

25. The system of claim 1, wherein the antennas connected to the at least one radio frequency identification reader are positioned in an array characterized by Cartesian coordinates.

26. The system of claim 1, wherein said radio frequency identification reader is capable of writing information to said radio frequency identification tags.

27. A method of analyzing a biological sample in a system comprising an automated analyzer, the method comprising the steps of:
   (a) providing a biological sample in a container having a radio frequency identification tag associated therewith;
   (b) interrogating a radio frequency identification tag on at least one container containing said biological sample to obtain information therefrom relating to storage information, wherein said interrogating is carried out by means of a radio frequency identification reader, and said radio frequency identification reader is capable of reading signals from a plurality of antennas, said plurality of antennas disposed in a plurality of banks of antennas, each bank of antennas capable of being attenuated at a different power level, whereby physical differences in between antennas and radio frequency identification tags can be compensated for;
   (c) comparing the storage information to a set of acceptable storage conditions; and
   (d) rejecting or accepting the sample container for analysis of the sample, based on the comparing step performed in (c),
   wherein steps (b), (c) and (d) are automatically performed by an automated analyzer system.

28. The method of claim 27, wherein said radio frequency identification reader is further capable of writing information to said radio frequency identification tag and said radio frequency identification reader writes information to said radio frequency identification tag.

29. The method of claim 27, further comprising the step of performing at least one analysis of the biological sample.

30. The method of claim 29, wherein the at least one analysis is performed with at least one instrument selected from the group consisting of automated immunoassay instruments, automated clinical chemistry instruments, automated hematology instruments, automated nucleic acid analyzer instruments, automated slide processing instruments, and automated protein analyzer instruments.

31. The method of claim 27, further comprising updating an information database to specify the location of each sample container present in the automated analyzer system.

32. The method of claim 27, further comprising updating the information database to specify the quantity of liquid removed from each sample container present in the automated analyzer system.

33. A method of automated analysis of a biological sample in an automated analyzer system comprising the steps of:
   (a) providing at least one reagent in a container having a radio frequency identification tag associated therewith, wherein the radio frequency identification tag comprises an information device that contains information on storage conditions to which the reagent container has been exposed;
   (b) interrogating a radio frequency identification tag on said at least one reagent container to determine the information on storage conditions for the at least one reagent container, wherein said interrogating is carried out by means of a radio frequency identification reader, and said radio frequency identification reader is capable of reading signals from a plurality of antennas, said plurality of antennas disposed in a plurality of banks of antennas, each bank of antennas capable of being attenuated at a different power level, whereby physical differences in between antennas and radio frequency identification tags can be compensated for;
   (c) comparing the information on storage conditions to a set of acceptable storage conditions; and
   (d) rejecting or accepting the reagent container for use in an automated analyzer system, based on the comparing step performed in step (c),
   wherein steps (b), (c) and (d) are automatically performed by an automated analyzer system.

34. The method of claim 33, wherein said radio frequency identification reader is further capable of writing information to said radio frequency identification tag and said radio frequency identification writes information to said radio frequency identification tag.

35. The method of claim 33, further comprising the step of performing at least one automated analysis of the sample using at least one reagent container determined to be acceptable for use.

36. The method of claim 35, wherein the at least one automated analysis is performed with at least one instrument selected from the group consisting of automated immunoassay instruments, automated clinical chemistry instruments, automated hematology instruments, automated nucleic acid analyzer instruments, automated slide processing instruments, and automated protein analyzer instruments.

37. The method of claim 33, further comprising the step of updating an information database to specify location of each reagent container present in the automated analyzer system.

38. The method of claim 33, further comprising the step of updating an information database to specify the quantity of sample removed from each sample container present in the automated analyzer system.

* * * * *